(12) United States Patent
Diaz

(10) Patent No.: US 9,311,809 B2
(45) Date of Patent: Apr. 12, 2016

(54) SYSTEM AND METHOD FOR IMPROVING HAND HYGIENE

(71) Applicant: Marc Howard Diaz, Plantation, FL (US)

(72) Inventor: Marc Howard Diaz, Plantation, FL (US)

( * ) Notice: Subject to any disclaimer, the term of this patent is extended or adjusted under 35 U.S.C. 154(b) by 0 days.

(21) Appl. No.: 13/923,907

(22) Filed: Jun. 21, 2013

(65) Prior Publication Data

US 2014/0375457 A1  Dec. 25, 2014

(51) Int. Cl.
| | |
|---|---|
| *G08B 23/00* | (2006.01) |
| *G08B 21/24* | (2006.01) |
| *A61L 2/00* | (2006.01) |
| *A47K 5/12* | (2006.01) |
| *G06F 19/00* | (2011.01) |

(52) U.S. Cl.
CPC ............... *G08B 21/245* (2013.01); *A47K 5/12* (2013.01); *A61L 2/0088* (2013.01); *G06F 19/327* (2013.01)

(58) Field of Classification Search
CPC . G08B 21/245; G06F 19/327; G06F 19/3493; A61L 2/0088; A47K 5/12
USPC ......... 340/573.1, 309.16, 691.6, 692, 539.13; 705/2
See application file for complete search history.

(56) References Cited

U.S. PATENT DOCUMENTS

| | | | |
|---|---|---|---|
| 5,610,589 A * | 3/1997 | Evans et al. ................. | 340/573.1 |
| 6,426,701 B1 * | 7/2002 | Levy et al. .................. | 340/573.1 |
| 7,542,586 B2 | 6/2009 | Johnson | |
| 8,249,295 B2 | 8/2012 | Johnson | |
| 8,294,584 B2 | 10/2012 | Plost | |
| 8,294,585 B2 | 10/2012 | Barnhill | |
| 2006/0273915 A1 * | 12/2006 | Snodgrass ................... | 340/573.1 |
| 2007/0015552 A1 * | 1/2007 | Bolling ....................... | 455/575.6 |
| 2008/0136649 A1 | 6/2008 | Van De Hey | |
| 2009/0267776 A1 | 10/2009 | Glenn | |
| 2009/0276239 A1 | 11/2009 | Swart et al. | |
| 2010/0134296 A1 | 6/2010 | Hwang | |
| 2010/0164728 A1 * | 7/2010 | Plost ............................ | 340/573.1 |
| 2010/0315243 A1 | 12/2010 | Tokhtuev | |
| 2011/0254682 A1 | 10/2011 | Sigrist | |
| 2011/0291840 A1 * | 12/2011 | Pelland et al. .............. | 340/573.1 |
| 2012/0212582 A1 | 8/2012 | Deutsch | |
| 2013/0229276 A1 * | 9/2013 | Hunter .................. | G08B 21/245 340/501 |
| 2014/0333744 A1 * | 11/2014 | Baym .................. | G08B 21/245 348/77 |

* cited by examiner

*Primary Examiner* — Thomas Mullen
(74) *Attorney, Agent, or Firm* — The Concept Law Group, P.A.; Scott D. Smiley; Mark C. Johnson

(57) ABSTRACT

A hand hygiene module and method of instructing and monitoring compliance of a hand hygiene event include a sanitizer dispensing device and the steps of identifying an initiation of a use of the sanitizer dispensing device and actively sequentially providing a plurality of stimuli to a user during the use of the sanitizer dispensing device, the plurality of stimuli including at least one of an audible signaling and a visual signaling and actively sequentially instructing each of a plurality of hygiene steps.

17 Claims, 13 Drawing Sheets

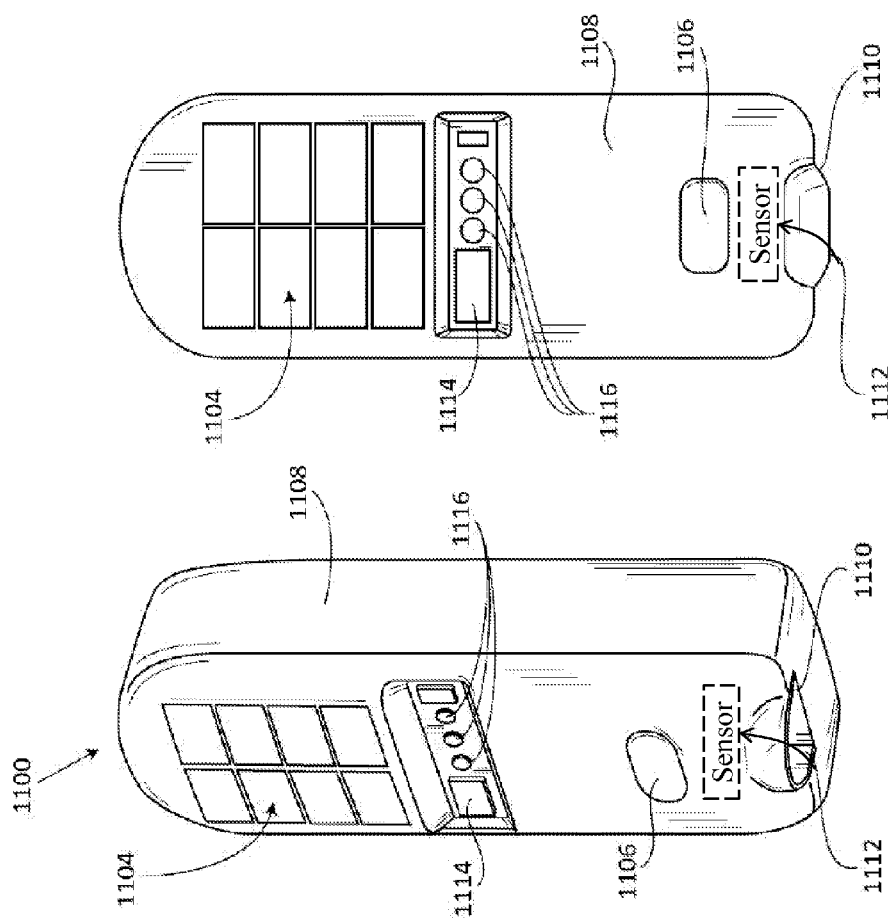

SYSTEM AND METHOD FOR IMPROVING HAND HYGIENE

FIELD OF THE INVENTION

The present invention relates generally to the art of hand sanitization and, more particularly, relates to a system and method for improving hand hygiene by encouraging the successful conversion of hand sanitation opportunities and performance of proper hand hygiene steps.

BACKGROUND OF THE INVENTION

Hand hygiene noncompliance is a serious health concern around the world that plagues hospitals, other health care environments, schools, food handling operations, and many others. In fact, hand hygiene noncompliance is the leading cause of hospital acquired infections (HAIs), which affect millions of patients every year. In some studies, HAIs are the majority cause of all infection-based hospital deaths each and every year. This is particularly troublesome due to the reality that patients who acquire HAIs were not admitted to the hospital or healthcare facility with the HAI but instead contracted the infection at the hospital or healthcare facility due to poor hygiene.

A major contributing factor for HAIs is a combination of hospital employee complacency and visitor ignorance. Specifically, a leading cause of HAIs is the result of physicians, nurses, other healthcare providers, and patients' guests' failure to properly sanitize their hands between touching hospital surfaces prior to interacting with other patients. Commonly, individuals either do not know of the proper hand hygiene steps, or the individuals do not use care to sanitize their hands at each step for the appropriate length of time. In addition, while staff members receive training and education on hand hygiene, visitors do not receive any training or education beyond passive dispensers and passive placards not coupled with the passive dispensers.

There are many types of hand hygiene compliance monitoring systems and methods today that monitor dispensing of hand sanitizer. Several known monitoring systems, such as U.S. Pat. Nos. 8,294,584; 8,294,585; 8,249,295; and 7,542,586; and Publication Nos. 2012/0212582; 2009/0276239; 2010/0315243; and 2008/0136649, teach methods for monitoring practices for better hand hygiene habits, but they do not provide for a related but unresolved problem, inter alia, the insufficient encouragement and inefficient instruction related to carrying out proper hand hygiene procedures. For example, known systems do nothing to attract attention and are, therefore, easy to walk past without using. While some hospitals post passive information placards to instruct visitors about hand sanitization, the placards are not attention grabbing, which causes patients, doctors, nurses, and the like to overlook them. The prior art systems, therefore, fail to provide individuals with instructions on carrying out hand hygiene procedures, such as teaching the individual steps of a proper hand hygiene process. Moreover, the prior hand hygiene compliance monitoring systems are not adaptable to changing environments. In addition, the prior hand hygiene compliance monitoring systems are stationary, which cannot be placed, for example, next to the bedside of a patient, allowing the patient to monitor staff and visitor compliance before coming into contact with the patient.

Further, the prior art systems do not differentiate between sanitation events or conditions. All uses of the sanitization devices are treated equally regardless of vastly different outcomes of failure or success. That is, failure to sanitize in an acute patient room is treated the same as a failure to sanitize while treating an immune suppressed patient. In addition, the known prior-art systems are not able encourage increased use and pass/fail monitoring criteria in accordance with changing conditions in the environment such as, for example, an epidemic, flu season, or other conditions.

Therefore, a need exists to overcome the problems with the prior art as discussed above.

SUMMARY OF THE INVENTION

The invention provides a sanitation system and method for improving hand hygiene that overcomes the hereinafore-mentioned disadvantages of the heretofore-known devices and methods of this general type and that monitor compliance of specific steps in the hand hygiene event and then alert the user, or other authority, if compliance of a particular step within the hand hygiene event is outside of a threshold range of compliant criteria.

With the foregoing and other objects in view, there is provided, in accordance with the invention, a system and method for attracting attention to convert opportunities for users to sanitize their hands and then monitoring hand hygiene compliance, where the method includes the steps of providing a sanitizer dispensing device, identifying an initiation of a use of the sanitizer dispensing device, and actively sequentially providing a plurality of stimuli, e.g., a series of pictures of video clips, to a user during the use of the sanitizer dispensing device, the plurality of stimuli including at least one of an audible signaling and a visual signaling, i.e., the series of pictures or video, which can include sound, and teaching a plurality of hygiene steps.

In accordance with another embodiment, the present invention includes electronically monitoring the user's compliance with the plurality of hygiene steps and recording the user's compliance with the plurality of hygiene steps and/or communicating an indicator of the user's compliance with the plurality of hygiene steps and then displaying an indicator of the user's compliance with the plurality of hygiene steps.

In accordance with a further embodiment of the present invention, the indicator of the user's compliance includes at least one of a user-compliant indication and a user-noncompliant indication.

In accordance with yet another embodiment, the present invention includes communicating with a wearable device, e.g., a badge, the badge having a visual indicia with at least two states, and placing the badge into one of the at least two states after electronically monitoring the user's compliance with the plurality of hygiene steps.

In accordance with an additional embodiment of the present invention, the badge is operable to communicate through a wireless protocol and, subsequent to the hand hygiene event, indicates the user's compliance with the plurality of hygiene steps.

In accordance with still a further embodiment, the present invention includes identifying the presence of a person in proximity to the sanitizer dispensing device and providing a changing stimulus output as a distance between the sanitizer dispensing device and the person changes.

In accordance with another feature, an embodiment of the present invention includes a system for facilitating and monitoring a hand hygiene process that includes a hand sanitization module including an display operable to selectively and sequentially depict a plurality of hand hygiene steps to a user, the plurality of hand hygiene steps together corresponding to a hand hygiene event. The system also includes a detector operable to detect a user's compliance with the plurality of hand hygiene steps, which can be performed by identifying the user's hand movements and comparing them to prescribed model hand motions or can be performed by monitoring the user's presence in front of the device for a time sufficient to have carried out the necessary hand motions.

In accordance with a further feature, an embodiment of the present invention includes a badge that has a receiver operable to receive information identifying the user's compliance with the plurality of hand hygiene steps and at least one indicator operable to communicate the user's compliance with the plurality of hand hygiene steps.

In accordance with a further feature, an embodiment of the present invention includes a visitor's badge/pass printing/issuing module and a controller operable to prevent the badge printing/issuing module from issuing the visitor's badge until subsequent to a detection of the user's compliance with the plurality of hand hygiene steps.

Although the invention is illustrated and described herein as embodied in a sanitization method for improving hand hygiene, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 11 is a perspective view of an embodiment of a hand hygiene module in accordance with one embodiment of the present invention;

FIG. 12 is a front view of the hand hygiene module of FIG. 11 in accordance with one embodiment of the present invention;

DETAILED DESCRIPTION

Figure 1:
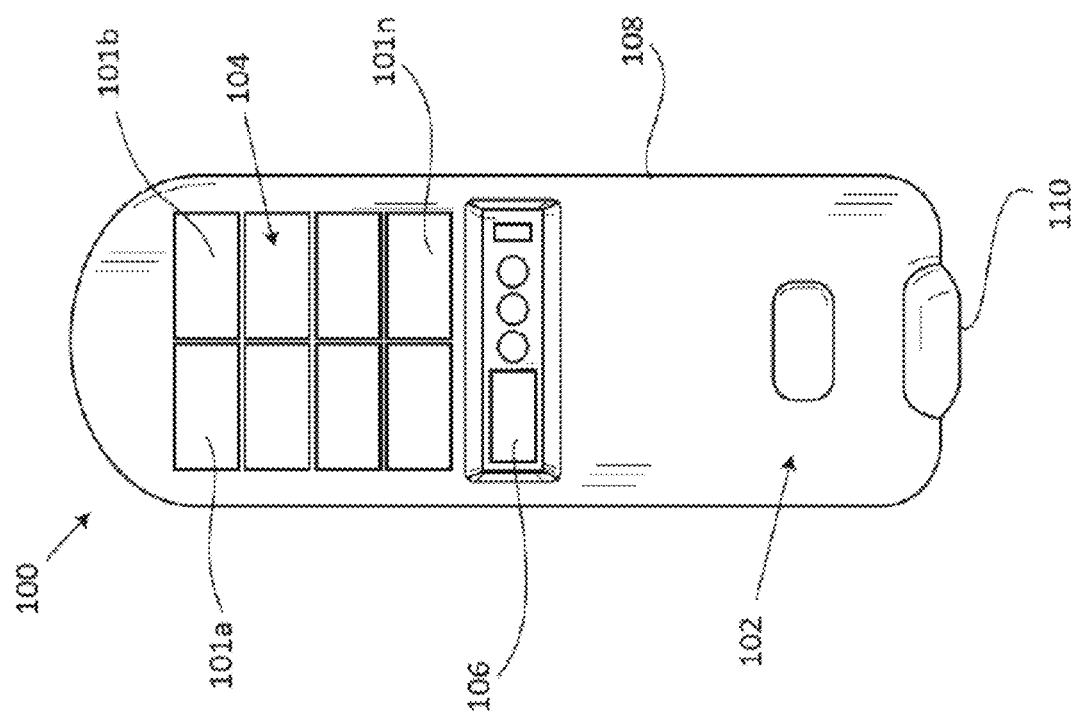
FIG. 1 is a perspective front view of a hand hygiene module in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient method of indicating compliance of a hand hygiene event, the hand hygiene event having a plurality of hand hygiene steps. The invention further relates to improving a hand hygiene event by assessing, in some embodiments, each of the plurality of hand hygiene steps and determining whether each of the steps are in compliance with good hand hygiene practices. Indication of a noncompliant hand hygiene event may have various results, for reasons discussed herein.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. FIG. 1 depicts an exemplary hand hygiene module 100 that includes an integrated hand sanitizer unit 102. In some embodiments, the hand hygiene module 100 is separate from the sanitizer unit 102. In the embodiment shown in FIG. 1, the hand hygiene module 100 has a teaching surface 104 that includes a plurality of images 101a-n ("n" is any number greater than 1), for instructing a person, or "user," how to properly sanitize their hands during a hand hygiene event. The person may include without limitation, a doctor, nurse, hospital staff member, health care worker, home health caregiver, patient, or patient's family member and/or friend. In some embodiments, the hand hygiene module 100 may include a digital display, which may include the plurality of images 101a-n, for teaching the person how to properly sanitize their hands. In some embodiments, the hand hygiene module 100 may include an e-ink display (not shown) for teaching the person how to properly sanitize their hands and/or display additional information such as power levels. In some embodiments, the teaching surface 104 lists a plurality of hand hygiene steps through indicia printed or otherwise affixed to the teaching surface, which can be viewed by those persons passing by the hygiene module 100. The hand hygiene module 100 instructs individuals on the procedures and steps for the hand hygiene event. In some embodiments, an indicia placard may form the teaching surface 104. The teaching surface 104 may be comprised of a material that is entirely, or partially, transparent or translucent, such as glass or plastic, to permit a backlit display for individually illuminating each of the plurality of hand hygiene steps, or alternatively, illuminating all the hand hygiene steps at the same time. Embodiments of the present invention that utilize the individually illuminating steps or other ways of indicating to a user that a step is or should be complete and a next step should be started is referred to herein as an indicator that communicates "actively sequentially." In other words, placards or other indicia/signaling elements that operate "actively sequentially" are differentiated from a simple passive sign with multiple steps shown all at once. The hand hygiene module 100 may be outfitted with various equipment, capabilities, and options that are dependent on the environmental conditions in which it is positioned. The hand hygiene module 100 adapts its stimuli to the physical environment, including the hallways, nodes, entrance ways, and the like.

The hand sanitizer unit 102 of the hand hygiene module 100 also includes a dispensing portion 110, through which one of a variety of materials may be dispensed. The materials can be hand sanitizing gel or one of many other materials that can be used for disinfecting a user's hands, other body parts, equipment, clothes, and others.

Figure 2:
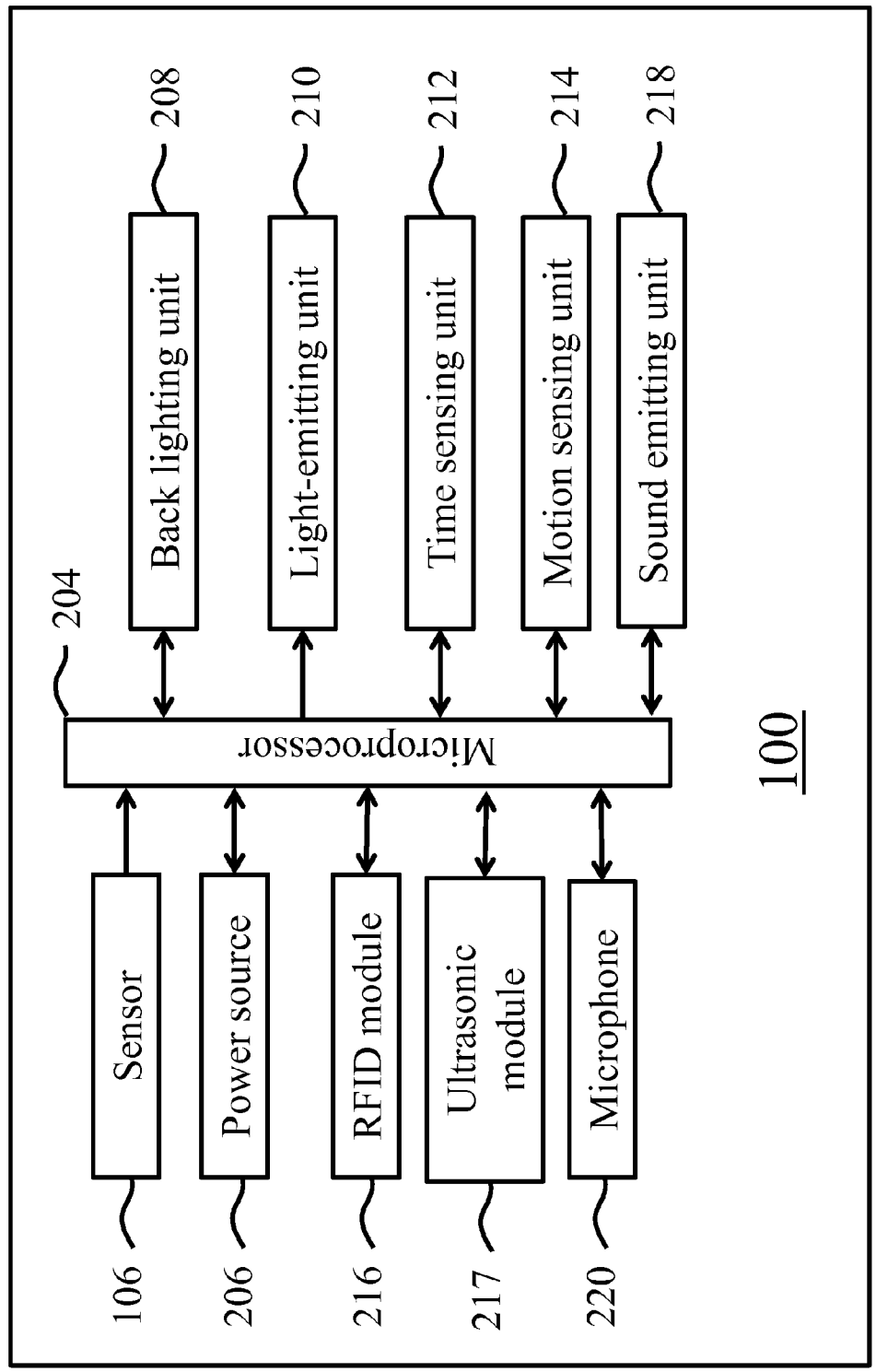
FIG. 2 is a block diagram of the hand hygiene module shown in FIG. 1 in accordance with the present invention.
Figure 3:
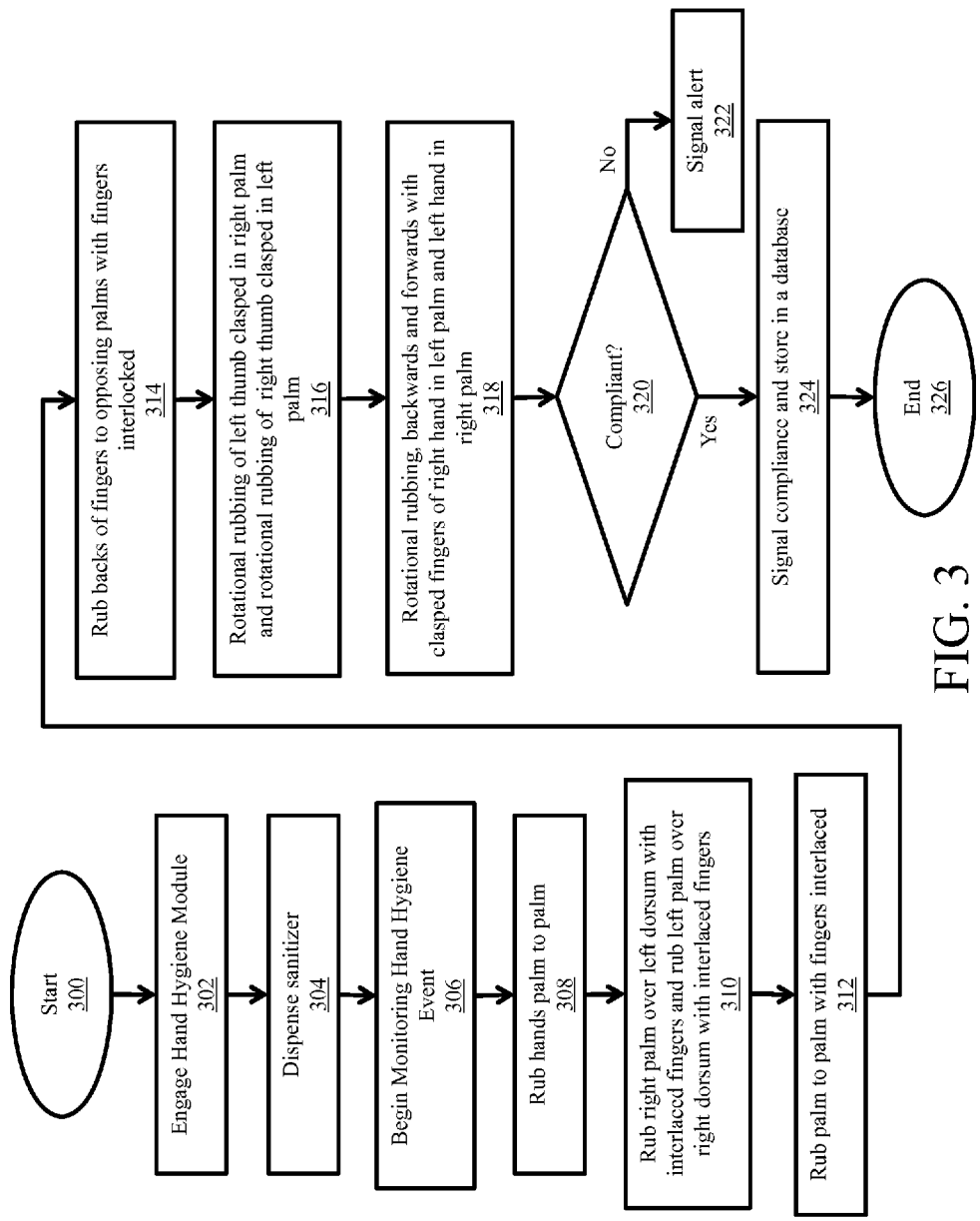
FIG. 3 is a process flow diagram illustrating a method of hand hygiene in accordance with the principles of the present invention.
Figure 4:
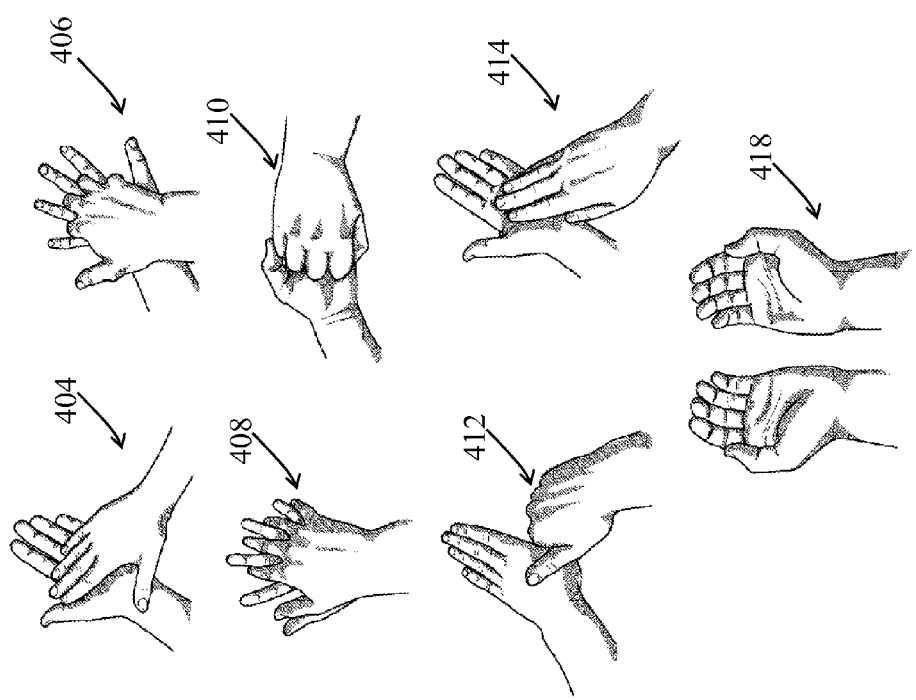
FIG. 4 is an illustration of a teaching surface connected with FIG. 1 in accordance with one embodiment of the present invention.

Referring to FIGS. 1 and 2, the hand hygiene module 100 includes a sensor 106. The sensor 106 is secured within the body 108 of the hand hygiene module 100, but can be in other locations or separate from the body in other embodiments. The body 108 includes a translucent portion for allowing the sensor 106 to sense/capture hand movement of the person. The sensor 106 may be a motion sensor employed to detect any motion and may also be utilized in connection with a microprocessor 204. The sensor 106 may include without limitation any type of known sensors for detecting bodily movement, such as passive infrared sensors, cameras, or the like. In some embodiments, the sensor 106 is an ultrasonic sensor which is particularly useful for detecting objects and measuring their distance. The ultrasonic sensor is capable of covering a broad area making it particularly useful when implemented with the instant hand hygiene module 100 because the hand hygiene module, along with one or more ultrasonic sensors, may be placed in areas that requires 360 degrees of two dimensional monitoring, as well as monitoring for a third dimension to account for variations in the height of individuals including tall individuals, small children, and wheelchair bound individuals. The microprocessor 204 may also be coupled in electrical communication with a power source 206, a back-lighting unit 208, a light-emitting unit 210, a time sensing unit 212, an RFID module 216, and ultrasonic module 217, and a motion-sensing unit 214, to name just a few. In other embodiments, the microprocessor 204 may work together with a microcontroller.

Still referring to FIGS. 1 and 2, in some embodiments the hand hygiene module 100, the plurality of images 101a-n includes guided instructions for teaching persons the proper hand hygiene steps for the hand hygiene event. The plurality of images 101a-n includes indicia for teaching or otherwise educating the proper hand movement at each step and the next image is displayed at the completion of the previous hand hygiene step. The indicia at each hand hygiene step may further educate the user on the appropriate period of time that the user should spend sanitizing their hands at the step. For example, the indicia may indicate that one hand hygiene step requires ten seconds of rubbing while another hand hygiene step requires fifteen seconds. The teaching surface 104 may be coupled with the back lighting unit 208 such that the hand hygiene steps illuminate sequentially to educate the person sanitizing their hands of the proper hand hygiene steps. While the instant invention discusses illuminating the teaching surface 104 at each step via a back lighting unit 208, it is not so required. It instead is merely one example to draw stronger attention to the active indicia during the time period during which a particular hand hygiene step is active. Thus, each step may be highlighted, for example, by an emission of fluorescent or iridescent lighting at the times selected by the timing unit 212. The timing unit 212 measures the appropriate time for each hand hygiene step thereby causing the back lighting unit 208, or other illumination member, to properly illuminate each hand hygiene step sequentially at specified time intervals. In use, the illumination helps to teach and properly inform the person of the appropriate length of time that each step requires. Positive stimuli is provided to reinforce engagement with the hand hygiene module 100 and/or compliance with the hand hygiene event, as well as to reward hand hygiene compliance. Alternatively, a negative stimuli is provided to reinforce engagement with the hand hygiene module 100 and/or noncompliance with the hand hygiene event. The positive and negative stimuli may include sound and/or light for users and others to hear and see thereby creating psychological pressure to engage the hand hygiene module and to comply with the hand hygiene event.

Referring now to FIGS. 1-4, a hand hygiene event includes step-by-step instructions (exemplified in FIG. 3) embodied in a plurality of hand hygiene steps depicted on the hand hygiene module 100. The process starts at 300 and immediately proceeds to step 302 where a person engages the hand hygiene module 100. The light-emitting unit 210 and or the sound-emitting unit 218 (shown in FIG. 2) may emit lights and sounds to draw attention to a passerby. The light-emitting and sound-emitting units 210, 218 are configured to draw strong attention to the hand hygiene module 100 for alerting the user of the presence of the hand hygiene module 100. In operation, a motion sensing unit 214 may sense the presence of a passerby for causing the light-emitting and/or sound-emitting units 210, 218 to emit light and sound sufficient to draw attention to user. The light-emitting unit 210 may become brighter as the motion sensing unit 214 senses the passerby nearing the hand hygiene module 100. Similarly, the sound-emitting unit 210 may become louder as the motion sensing unit 214 senses the passerby near the hand hygiene module 100. In some embodiments, the hand hygiene module 100 may increase attention stimuli and alerts as the motion sensing unit 214 detects an increase in the distance between the hand hygiene module 100 and the passerby. The hand hygiene module 100 may also communicate a variety of aural and visual stimuli to engage and otherwise draw attention to the hand hygiene module 100 or to alert the user or other person of a compliant hand hygiene event. For example, in one embodiment the lights can flash en bloc, i.e., as a unit. In other embodiments, the lights can flash in a pattern.

In alternative embodiments different noises, such as voice messages, can be implemented to draw attention to the hand hygiene module 100. The voice messages may be broadcast anywhere from a few seconds to a few minutes, or longer. The messages could also be broadcasted on a continuous loop. A plurality of messages could also be played at various time intervals. In some embodiments, message broadcasts may be keyed off of the motion sensing unit 214. The motion sensing unit 214 may detect pressure changes in a zone. For example, flushing a toilet or a door opening may change the pressure in a bathroom, thereby causing a message to be broadcast from the hand hygiene module 100. Additionally, a microphone 220 may also listen for sounds to indicate that a person is nearing the hand hygiene module 100. In some embodiments, the microphone 220 may listen for toilet flushing and/or doors opening and closing to cause the broadcast of one or more messages. The stimuli can be set to a random pattern to prevent staff from being accustomed to the stimuli. The stimuli may use prominent colors and symbols to increase awareness. The embodiments of the hand hygiene module 100 take advantage of the Hawthorne effect, which is known in the art, such that worker productivity increases because the worker is aware that they are being observed and monitored for hand hygiene compliance.

The process continues at step 304 with the sensor 106 detecting the presence of one or more hands positioned near the dispensing portion 110 of the hand sanitizer and dispensing sanitizing fluid. The hand hygiene module 100, reacting to detection of one or more hands near the dispensing portion, may illuminate, or otherwise draw attention to the teaching surface 104. One way for drawing attention to the teaching surface 104 may include illuminating at least a portion of the teaching surface 104. The hand hygiene device may additionally output an audible message and/or instructions to teach the user how to appropriately sanitize one's hands. In some embodiments, the sensor 106 may additionally initiate, or otherwise cause, sanitizer to be dispensed from the hand hygiene module 100. The user should receive enough sanitizer so that the sanitizer can be distributed to cover all hand surfaces.

Next, at step 306 the hand hygiene event timer is commenced. Timing unit 212 begins measuring the start of the hand hygiene event. One purpose of the timing unit 212 is for communicating with the microprocessor 204 to cause a visual or audible alert, thereby indicating the completion of the hand hygiene event. In some embodiments, the timing unit 212 measures the time that the user spends in front of a hand hygiene module to determine compliance with the hand hygiene event whereby compliance is merely the measure of time spent in front of the hand hygiene module. A noncompliant alarm may be a warning from the hand hygiene module or pre-set alarm on a badge 800, in accordance with the teachings of the present embodiment.

After step 306, the process continues to step 308 wherein a first hand hygiene step 404 is the active step that teaches, or otherwise instructs, the individual. This first active step may teach the individual to rub their hands palm to palm. Attention is drawn to the active step shown on the teaching surface 104. The teaching surface 104 may be configured to draw the user's attention to the active step. In some embodiments, this may be accomplished by backlighting the active step, such that the first hand hygiene step 404 is distinguishable from the other hand hygiene steps. In some embodiments, this may be accomplished by illuminating the active step against the remaining teaching surface 104. In some embodiments, attention may be drawn to the active step by outlining the active step with an illumination. In some embodiments, an audible instruction may draw attention to the active step thereby permitting the entire teaching surface 104 to be illuminated if desired. In still other embodiments, a video display is used to display each step serially, e.g., with a video, and can also provide audible instructions.

Step 310 includes a second hand hygiene step 406 being the active step that teaches, or otherwise instructs, the individual. At step 310, the user is taught to rub their right palm over left dorsum with interlaced fingers, and to rub their left palm over right dorsum with interlaced fingers. As is known in the art, a dorsum is an upper surface of an appendage. Attention is drawn to the active step shown on the teaching surface 104. The teaching surface 104 may be configured to draw user attention to this active step. In some embodiments, this may be accomplished by backlighting the active step, such that this active step is distinguishable from the other hand hygiene steps. In some embodiments, this may be accomplished by illuminating the active step against the remaining teaching surface 104. In some embodiments, attention may be drawn to the active step by outlining the active step with an illumination. In some embodiments, an audible instruction may draw attention to the active step, thereby permitting the entire teaching surface 104 to be one of illuminated and dulled.

The process continues to step 312 wherein a third hand hygiene step 408 is now the active step that teaches, or otherwise instructs, the individual. At step 312, the active step teaches the individual to rub their hands palm to palm with their fingers interlaced. Attention is drawn to the active step shown on the teaching surface 104. The teaching surface 104 may be configured to draw user attention to this active step. In some embodiments, this may be accomplished by backlighting the active step, such that this active step is distinguishable from the other hand hygiene steps. In some embodiments, this may be accomplished by illuminating the active step against the remaining teaching surface 104. In some embodiments, attention may be drawn to the active step by outlining the active step with an illumination. In some embodiments, an audible instruction may draw attention to the active step, thereby permitting the entire teaching surface 104 to be illuminated if desired.

At step 314, a fourth hand hygiene step 410 is now the active step that teaches, or otherwise instructs, the individual. At step 314, the active step teaches the individual to rub the backs of their fingers to their opposing palms with their fingers interlocked. Attention is drawn to the active step shown on the teaching surface 104. The teaching surface 104 may be configured to draw user attention to this active step. In some embodiments, this may be accomplished by backlighting the active step, such that this active step is distinguishable from the other hand hygiene steps. In some embodiments, this may be accomplished by illuminating the active step against the remaining teaching surface 104. In some embodiments, attention may be drawn to the active step by outlining the active step with an illumination. In some embodiments, an audible instruction may draw attention to the active step, thereby permitting the entire teaching surface 104 to be illuminated if desired.

At step 316, a fifth hand hygiene step 412 is the active step that teaches, or otherwise instructs, the individual. At step 316, the active step teaches the individual to rotation rub having their left thumb clasped in their right palm and rotational rub having their right thumb clasped in their left palm. Attention is drawn to the active step shown on the teaching surface 104. The teaching surface 104 may be configured to draw user attention to this active step. In some embodiments, this may be accomplished by backlighting the active step, such that this active step is distinguishable from the other hand hygiene steps. In some embodiments, this may be accomplished by illuminating the active step against the remaining teaching surface 104. In some embodiments, attention may be drawn to the active step by outlining the active step with an illumination. In some embodiments, an audible instruction may draw attention to the active step, thereby permitting the entire teaching surface 104 to be illuminated if desired.

Proceeding now to step 318, a sixth hand hygiene step 414 is now the active step that teaches, or otherwise instructs, the individual. At step 318, the active step teaches the individual to rotation rub backwards and forwards with clasped fingers of the right hand in the left palm and rotation rub backwards and forwards with clasped fingers of the left hand in the right palm. Attention is drawn to the active step shown on the teaching surface 104. The teaching surface 104 may be configured to draw user attention to this active step. In some embodiments, this may be accomplished by backlighting the active step, such that this active step is distinguishable from the other hand hygiene steps. In some embodiments, this may be accomplished by illuminating the active step against the remaining teaching surface 104. In some embodiments, attention may be drawn to the active step by outlining the active step with an illumination. In some embodiments, an audible instruction may draw attention to the active step, thereby permitting the entire teaching surface 104 to be illuminated if desired. Some embodiments may include step 416 instructing that the hands must be dry to properly complete the hand hygiene event.

The process continues to step 320, wherein the hand hygiene module 100 determines whether the user has complied with each step in the hand hygiene event. If the hand hygiene event is noncompliant, a noncompliant signal (i.e., a user-compliant indication), depicted in step 322 may be activated. In one embodiment, the noncompliant signal may directly alert an authority, such as a hospital staff member charged with monitoring hand hygiene compliance. The noncompliant signal may be sent via a wireless communication. For example, the noncompliant signal may send an email to alert the hospital staff member of the noncompliance. For another example, the noncompliant indication may be wirelessly transmitted to and stored on a database (not shown). Storing noncompliant indications on the database allows for monitoring of the zone of noncompliance. In many cases, particular zones in the hospital are more susceptible to spread of HAI than other zones. For example, patients in the intensive care unit (ICU) would generally be more susceptible to HAIs than patients in the discharge lounge zone. The noncompliant alert may include a noncompliant alarm on the hand hygiene module 100, the security badge 800 (disclosed below), or both. In some embodiments, a hospital staff member, or other supervisory staff member may be required to interact with the hand hygiene module 100 and/or the security badge 800 in order to turn off the noncompliant alarm.

In some embodiments, the noncompliant indications may be stored into a database that permits analytic identification of poorly performing compliance areas. This would allow the hospital to individually address a zone, or persons, performing poorly. The hand hygiene event may be scrutinized based on the level risk for HAI presented in that zone. The hospital may further alter their response to performance based compliance of the hand hygiene events for a particular zone based on endemic and/or epidemic infection rates. In addition to altering the response to the performance based compliance, the system permits calibration and alteration of the risk assessment and analysis factors wherein the risk factors may include, for example, endemics or epidemics in the wider community. More particularly, the hospital may alter their response based on the infection rates of the institution as a whole, or based on infection rates of particular zones and/or hospital units. In one embodiment, different devices and or badges can be weighted with multipliers to indicate the magnitude of a failure to sanitize or to not take enough time performing the sanitization process. For example, a device in a high risk area can count on failure as a factor of 3 while a device in a lower risk area can carry a weighted factor of 1. This can be dependent on factors such as location, staff function, etc.

Figure 14:
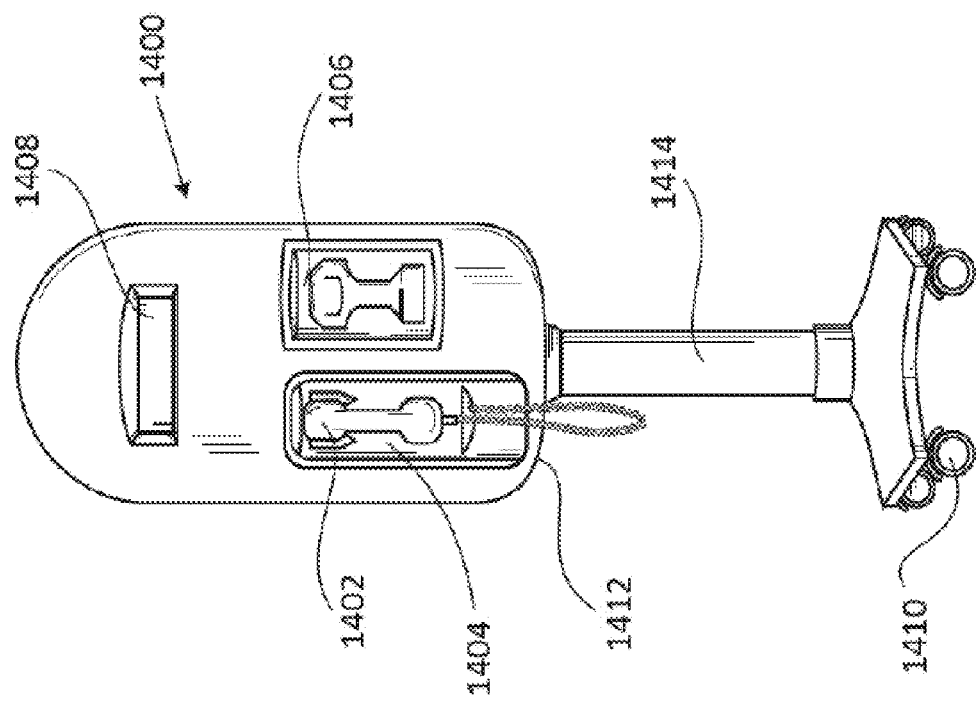
FIG. 14 is a perspective front view of a portable service area module.

Alternatively, the hand hygiene module 100 may determine that the hand hygiene event is compliant. A signal indicating compliance may be sent via a wireless communication. In some embodiments, the signal is sent via the phone on the service area module 1400 shown in FIG. 14. For example, the compliant signal may send an email to alert the hospital staff member of the compliance. For another example, the compliant indication may be wirelessly transmitted to and stored on a database (not shown). Storing compliant indications to the database allows for monitoring of the zone of compliance and/or noncompliance, and further allows for increased education for employees and staff that work in zones showing poor hand hygiene performance. The process may then terminate at step 326. The noncompliant indication, in accordance with the Hawthorne effect, should be observable to others thereby creating a social pressure and obligation to properly sanitize. In some embodiments, there is a compliant/noncompliant indication. The service area module 1400, shown in FIG. 14, is used for the purpose of compliance indications. The phone will flash with a light and make a sound to prompt staff to answer the phone. In one embodiment, the flashing light and sound cannot be turned off until the phone 1402 is answered to ensure that staff are aware of their level of compliance.

Figure 5:
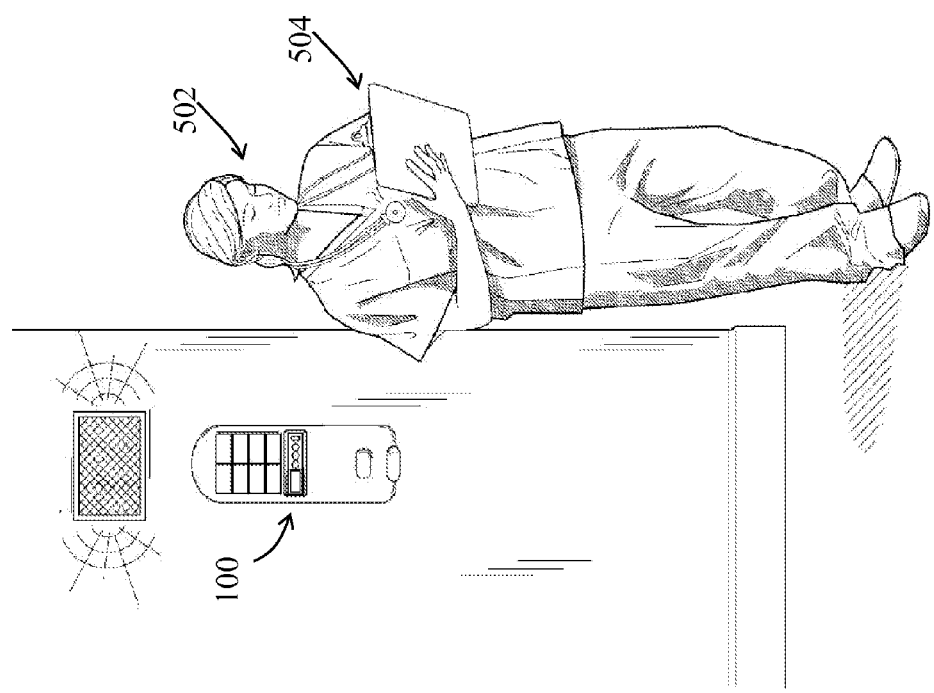
FIG. 5 illustrates the hand hygiene module of FIG. 1 having variable attention stimuli in accordance with one embodiment of the present invention.

Referring now to FIG. 5, attention stimuli, such as volume and/or luminance, may be altered, either up or down, on the hand hygiene module 100 for drawing increased attention to the unit. In some embodiments, this may occur with interaction with the light-emitting unit 210 and/or sound emitting unit 218. The attention stimuli may be adjusted, either automatically or manually, based for example on the time of the year, such as flu season, endemic infection levels, epidemic infection levels, and as further discussed in an embodiment shown in FIG. 11 disclosed herein. A central server (not shown) may wirelessly interact with the hand hygiene module 100 for causing the adjustment of attention stimuli. The central computer may be programmed by the infection control staff for causing calibration instructions to be sent or otherwise provided to the hand hygiene modules. In some embodiments the attention stimuli may be adjusted, up or down, based on the brightness of the zone. For example, a dimly lit zone would require attention stimuli that is less illuminant than a more brightly lit zone. In some embodiments, the attention stimuli may be adjusted, up or down, based on the risk values where the location of the hand hygiene module was placed. The hand hygiene module 100 can compensate for serial attention, such as a busy doctor 502 reading a chart. In use, a doctor 502 may need increased attention stimuli to remind them of their need to engage the hand hygiene module 100 and sanitize their hands, because the doctor may be concentrating and engaged in other work activities, such as reading patient charts 504. The attention stimuli can be adjusted to zero at night to avoid disrupting rest and relaxation of the patients. Each trip includes an entrance or a node and then progresses along a pathway ending at a final destination. Hand hygiene modules 100 are strategically placed along the path and uses differing stimuli to create multiple opportunities for hand sanitation. Because individuals respond differently to different stimuli, each of the hand hygiene modules 100 have a differing stimuli along the path.

Figure 6:
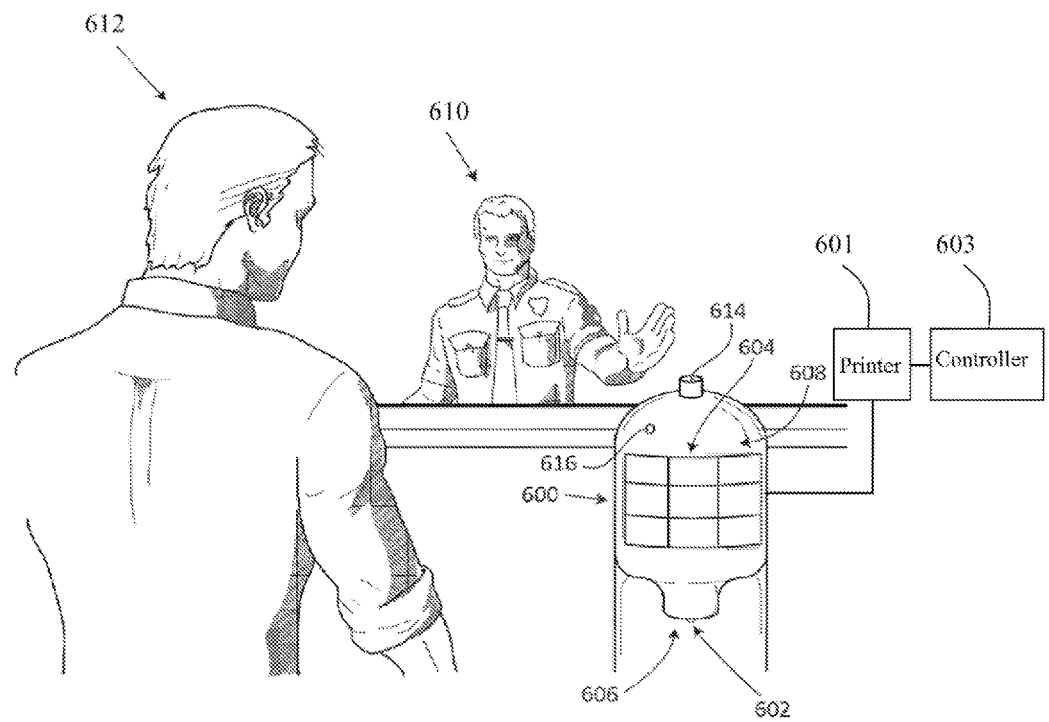
FIG. 6 illustrates a hand hygiene module configured for ensuring entrants to a hospital practice hand hygiene prior to entrance in accordance with one embodiment of the present invention.
Figure 7:
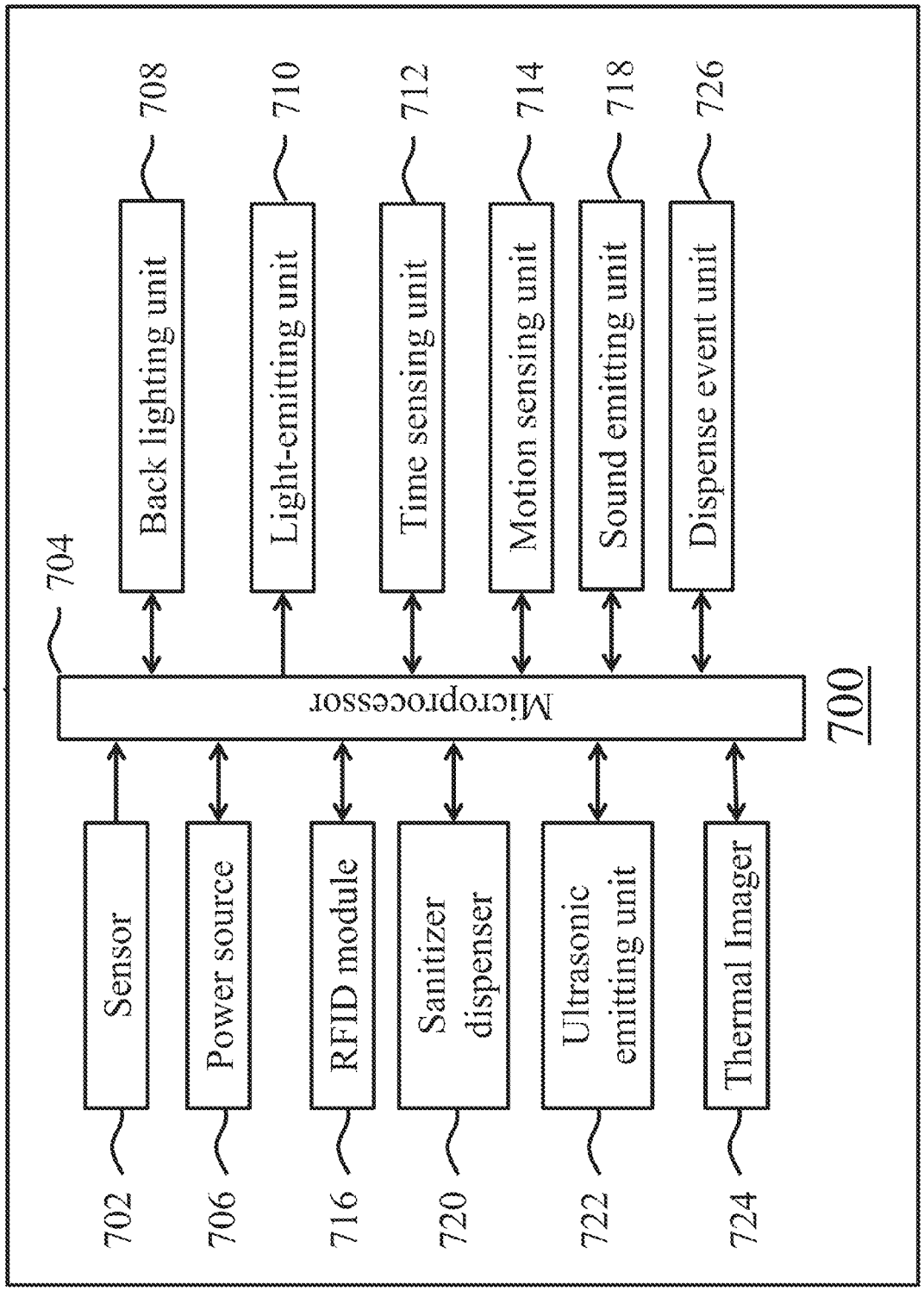
FIG. 7 is a block diagram of the hand hygiene module shown in FIG. 6 in accordance with one embodiment of the present invention.

Referring now to FIGS. 6 and 7, a hand hygiene module 600 includes a combination of a hand sanitizer dispenser 602 and a teaching surface 604 having a plurality of images that instructs a person how to properly sanitize their hands during a hand hygiene event. The sanitizer is stored within the body 608 of the hand hygiene module 600. The teaching surface 604 may be of a transparent or translucent material, such as a glass or plastic, to permit a backlit display for individually illuminating each of the plurality of hand hygiene steps, or the entire teaching surface 604 as a whole.

The hand hygiene module 600 may also include a sensor 702. The sensor 702 is secured within a body 608 of the hand hygiene module 600. The body 608 encloses the core components. The body may be coupled with a display for depicting various graphics. The graphics may depict, as only one example, a CDC/WHO-approved hand sanitization process. The graphics are not limited to the CDC/WHO-approved hand sanitization process and may depict any conceivable hand sanitization process. The display or other graphics may flash to attract attention, such as en bloc, in a sequential order, or in an alternating checkerboard pattern.

A thermal imager 724, such as an uncooled thermal imager, which can be within the hand sanitization device 600 or any other device, operates, in accordance with the goals of the present invention, to detect individuals with pyrexia, i.e. fever, in individuals such as doctors, nurses, and hospital visitors. If the thermal imager 724 detects pyrexia, individuals may be denied entry to the hospital, healthcare facility, or particular zones within the hospital/healthcare facility. In some embodiments, if the thermal imager 724 detects pyrexia, the individual may be assisted or admitted to the hospital. In addition to the thermal imager 724 for detecting pyrexia, some embodiments include a risk assessment feature that detects and calculates a present or future risk for cross contamination of infection based on a clinical area in relation to a person, place, or thing. In some embodiments, the risk assessment feature includes calculations based on a fourth dimension of space and time. The risk assessment feature allows infection control staff the ability to position hand hygiene modules in clinical care areas based on area risk factors and/or outside risk factors, such as epidemics of influenza in the wider community. Also risk assessment not only allows staff to reposition devices but to calibrate their attention getting stimuli, educational stimuli, and/or risk factor weighting.

The system takes into direct, or indirect consideration the continuum of hierarchies in an institution. Devices may be adjusted to account for higher environmental risk factors. Risk factors may be internal, such as the oncology, burn, and intensive care units where the magnitude of the risk associated with noncompliance of infection control procedures is higher, for example, than in normal acute care areas. Risk factors may be increased in areas having high endemic infection rates due to seasonal changes, such as during winter storms.

A dispense event counter 726, implemented via the microprocessor 704, records the hand hygiene events for the particular hand hygiene module 600. The hand hygiene module 600 may communicate with hospital staff, or otherwise transmit status information, to cue staff, or a third-party vendor, to the need to replace sanitizers, batteries, or a malfunctioning hand hygiene module 600.

The body 608 includes a translucent portion 606 for allowing the sensor 702 within the body 608 to capture hand movement of the person interacting with the hand hygiene module 700. The sensor 702 may also, or alternatively, be a motion sensor to detect any motion implemented by a microcontroller 704. The sensor 702 may include without limitation any type of known sensors for detecting body movement, such as passive infrared sensors, cameras, or the like. In some embodiments, the sensor 702 is an ultrasonic sensor. The sensor 702 may be configured to detect the presence of one or more hands. The sensor 702 may be configured to detect the presence of a person. The sensor 702 may be configured, inter alia, to detect and communicate wirelessly with a hand hygiene badge or identification badge, as further discussed herein. The body 608 may maintain an audio transducer for outputting sounds. The hand hygiene module 600 has a power source 706. The power source 706 may include batteries, an AC power source, or other known power sources for supplying charges to an electronic device. If the hand hygiene module 600 includes a battery, a battery status indicator 616 indicates the battery charge status. The battery may be located within the body of the hand hygiene module 600. For example, the light-emitting unit 710 may flash green to indicate good battery status and/or flash red to indicate that the battery charge has been depleted. An e-ink screen may be implemented to indicate depleted battery charge. The system may further be implemented by the microcontroller 704 coupled in electrical communication with a power source 706, a back lighting unit 708, a light-emitting unit 710, a time sensing unit 712 and a motion sensing unit 714, to name just a few. The sensor 702 further operates to dispense sanitizer from the detection of at least one hand placed under the sanitizer dispenser 720. The hand hygiene module 600 may include an ultrasonic emitter unit 722 that emits a communication signal to activate a hand hygiene badge (see FIGS. 8-9). The ultrasonic emitter unit 722 may be used to confirm sanitizer dispenser activation. The ultrasonic emitter unit 722 may further be used to transmit a time that a person, or their badge, spends in front of the hand hygiene module 600. In some embodiments, the time spent in front of the hand hygiene module 600 after activation evidences thoroughness of the hand hygiene event. Accordingly, the time spent in front of the hand hygiene module 600 may be used to determine compliance with the hand hygiene events, procedures, and displayed instructions.

In some embodiments, the system includes guided instructions for teaching persons the proper hand hygiene steps for the hand hygiene event. In some embodiments, the guided instructions may be provided with verbal and/or voice prompting for teaching the hand sanitization process. Each hand hygiene step has indicia for teaching or otherwise educating the proper hand movement at that step. The indicia at each step may further educate the user on the appropriate period of time that the user should spend sanitizing their hands at the step. The teaching surface 604 may be coupled with the back lighting unit 708 such that the hand hygiene steps illuminate sequentially to indicate and educate the person sanitizing their hands of the proper steps. While the instant invention discusses illuminating each step via a back lighting unit 708, it is not so required. It instead is merely necessary to draw a stronger attention to the active indicia during the time period during which a particular hand hygiene step is active. Thus, each step may be highlighted, for example, by an emission of fluorescent or iridescent lighting at the times selected by the timing unit 712. The timing unit 712 measures the appropriate time for each hand hygiene step thereby causing the back lighting unit 708, or other illumination member, to properly illuminate each hand hygiene step sequentially at specified time intervals.

In some embodiments, as shown in FIG. 6, the hand hygiene module 600 may be placed at or near a hospital entrance and/or visitor check-in locations. These locations are where visitors 612 commonly are screened and receive check-in passes, such as wristbands, badges and/or stickers. In some embodiments, a staff member 610, such as a security guard, must witness a person complete a compliant hand hygiene event. If the staff member witnesses successful completion of the hand hygiene event, the staff member can issue a check-in pass. A person in compliance with the hand hygiene event, the hand hygiene event having a plurality of hand hygiene steps, should include successfully sanitizing their hands for a specified period of time. That specified period of time may, in some embodiments, include spending a specified time sanitizing their hands at each step. The specified time for each hand sanitizing step may vary. The staff member will not issue a check-in pass until the visitor is compliant. Additionally, the staff member may not allow healthcare providers, such as doctors, nurses and other staff members, to pass through the hospital until a successful hand hygiene event is witnessed.

In one embodiment, shown in FIG. 6, the hand hygiene module 600 shall monitor the hand hygiene event through sensor 702. The hand hygiene module 600 shall signal, or otherwise notify, the staff member that the visitor, or other hospital entrant, has successfully complied with the hand hygiene event. In one example, the hand hygiene module includes signaling indicia 614, such as a green LED light, for signaling to the staff member that the hospital entrant is hand sanitizer compliant. In one embodiment, the hand hygiene module will use the length of time that the person is positioned near the hand hygiene module 600 to determine successful compliance. In other embodiments, the hand hygiene module 600 will actively monitor the hand motion to determine whether the motion of hand sanitization is in compliance with each hand hygiene step for the requisite period of time.

In some embodiments, the hand hygiene module 600 is communicatively coupled to a wearable device dispensing module 601, such as, for example, the front desk computers, check-in pass printer, or the like. The computer system and/or printer may include a controller 603 that will not issue a check-in pass, or otherwise authorize admittance to the hospital, until the hand hygiene module 600 signals a compliant hand hygiene event. For example, the hygiene module 600 may be integrated in the check-in pass printer. When a visitor is properly identified and cleared for entrance into the hospital by the guard, an indicator will signal to the visitor that their pass is ready to be printed. Before the printer will produce the visitor pass however, the visitor must properly utilize the hygiene module 600. This includes following the proper steps to become fully compliant.

Figure 9:
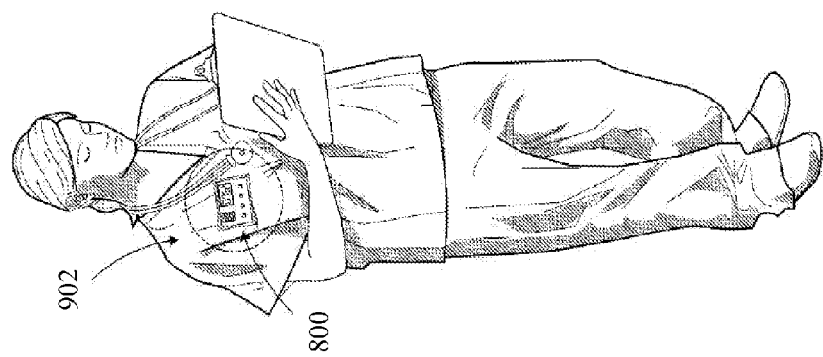
FIG. 9 illustrates the hand hygiene badge shown in FIG. 8 coupling with an article of clothing in accordance with one embodiment of the present invention.
Figure 8:
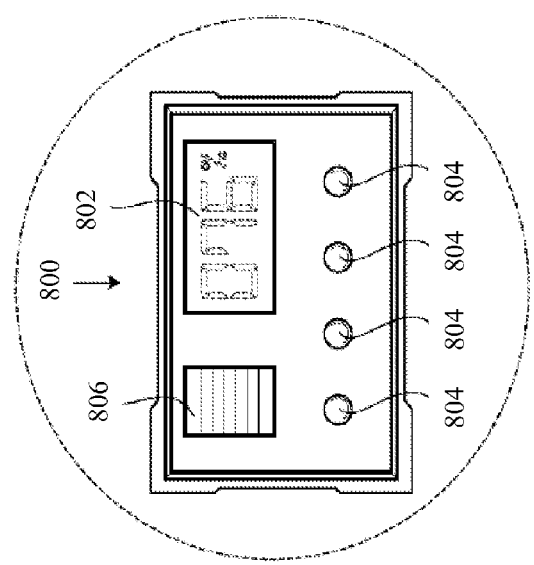
FIG. 8 is a front view of a hand hygiene badge in accordance with one embodiment of the present invention.

Referring now to FIGS. 8-9, a hand hygiene badge 800 is shown. The badge may include a microprocessor, microcontroller, RFID components, batteries, ultrasonic communication capabilities and other common electronic badge components. In some embodiments, the hand hygiene badge is combined with an identification badge, such as a check-in pass, employee identification badge, or the like. The badge may include identification indicia 806 for identifying the visitor or employee. The badge 800 may be removably affixed to an article of clothing 902. The hand hygiene badge 800 may be affixed to a lanyard or other known devices to affix badges to individuals or their persons. The hand hygiene badge may include attachment points (not shown) for attaching the hand hygiene badge 800 to a badge case, a clip, or a combination thereof. The hand hygiene badge 800 may include a display 802, such as a digital display, an e-ink display, or the like. The hand hygiene badge may be formed from an impact resistant casing for protecting the inner components. The display 802 can provide a variety of information. For example, the display 802 can display a percentage of compliance with required hand hygiene events over a determined time period. The time period could be any conceivable time period. The display 802 can display a percentage of the number of successfully converted hand hygiene events. The display 802 can display a percentage of the number of successfully converted hand hygiene events in relation to the number of opportunities to engage with a hand hygiene module for a hand hygiene event. The display can display a percentage relating to the number of hand hygiene modules that the staff member passes without engaging in a hand hygiene event. The display 802 can be implemented to indicate the battery level of the badge, particularly including a low battery level. In addition, the badge 800 can have a time interval unit 804, which may, in some embodiments, be formed as one or more lights 804 that indicate an average duration of hand sanitization events.

Figure 10:
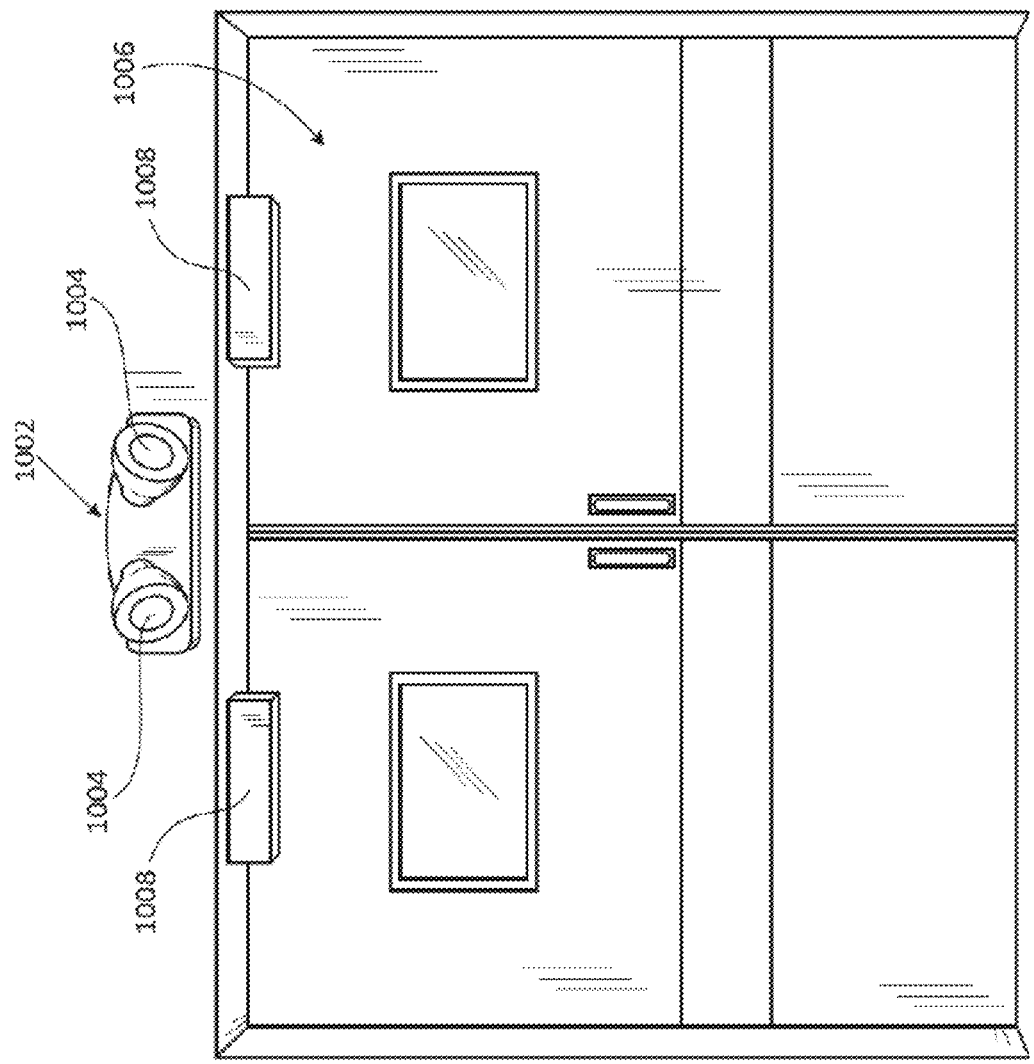
FIG. 10 illustrates a perspective front view of a badge communication sensor unit in accordance with one embodiment of the present invention.

Referring now to FIG. 10, a badge communication sensor unit 1002 is shown that may be placed in various zones within a building structure. The system includes one or more sensors 1004. The badge communication sensor unit 1002 may be placed in various locations, such as above doors 1006, hanging on a wall, on a portable stand, or near zone entrances. The badge communication sensor unit 1002 may be placed in any desired location. Zones may include hospital wings, individual patient rooms, and the like. The badge communication sensor unit 1002 may be configured to communicate with the hand hygiene badge 800. The badge communication sensor unit 1002 is configured to transmit and receive badge information. The received badge information can then be retransmitted to a service area module 1400. The service area module 1400 subsequently transmits the received badge information to a centralized computer. While the present embodiment provides a network of devices for delivering the badge information to the centralized computer, it is not so required. Instead, it is merely necessary to cause transfer of badge information to a centralized computer so that the infection control staff can monitor and review the badge information, thereby eliminating extra steps that commonly lead to non-compliance of workers and visitors alike. In some embodiments, the badge communication sensor unit 1002 may use infrared communication to transmit information to the hand hygiene badge 800, as well as communication with any additional device.

In some embodiments, the badge communication sensor unit 1002 may be configured to override a countdown sequence on hand hygiene badge 800 for alerting of a need for a hand hygiene event. The badge communication sensor unit 1002 may be placed in high risk areas. For instance, a particularly sick patient may be extremely susceptible to HAI. Thus, the badge communication sensor unit 1002 may cause the time interval to decrease faster. In some embodiments, the badge communication sensor unit 1002 may cause the time interval to override the present countdown and signal an immediate need for a hand hygiene event. Each time a badge passes by the sensor unit 1002, the time interval may be increased or decreased, as determined or as otherwise required under prescribed healthcare guidelines. The badge communication sensor unit 1002 is configured to communicate data received from the badges 800 to a service device area or other centralized computer.

In some embodiments, the badge communication sensor unit 1002 and/or the hand hygiene modules may receive information transmitted from the hand hygiene badge 800 to be ultimately transferred to a compliance server and/or database (not shown). The badge communication sensor unit 1002 may receive identification from the hand hygiene badge 800. Additionally, the badge may transmit hand hygiene event information to the compliance server. Reports may be generated for allowing compliance staff to determine individuals who are not complying with the hand sanitization compliance standards and/or guidelines.

In some embodiments, a magnetic door lock 1008 magnetically locks a door, such as a hospital wing door. The badge communication sensor unit 1002 is configured to read the hand hygiene badge 800. The badge communication sensor unit 1002 may check identification credentials to determine whether the individual associated with the hand hygiene badge 800 has the requisite credentials to enter through the doorway 1006. The badge communication sensor unit 1002 checks whether the individual associated with the hand hygiene badge 800 has complied with a required hand hygiene event. If the hand hygiene badge indicates that the previous hand hygiene event was noncompliant, or a determined period of time has lapsed since the last hand hygiene event, the door shall remain locked after the badge communication sensor unit 1002 communicates with the hand hygiene badge 800. The badge communication sensor unit 1002 may alert the individual of their need to sanitize their hands. The individual is able to near the hand hygiene module 600 to engage in a hand hygiene event. Subsequently, the individual may again approach the doorway 1006. The badge communication sensor unit 1002 will check whether the individual associated with the hand hygiene badge 800 is now compliant. If the hand hygiene badge 800 provides data indicating compliance, the magnetically locked door will unlock. It is contemplated that while a magnetic door lock is contemplated, other types of door locks may be instituted to accomplish the spirit and scope of the present invention.

In some embodiments, the badge communication sensor unit 1002 may be placed near the exits of hospitals for turning the time interval unit 804 on and off as persons enter and leave the hospital or other healthcare facility.

Referring now to FIGS. 11-12, a hand hygiene module 1100 is illustrated having a communication unit (not shown) within the body 1108 of the hand hygiene module 100 for detecting the presence of a hand hygiene badge 800 and communicating with said hand hygiene badge 800. The hand hygiene module 1100 may be portable, wherein the hand hygiene module 1100 may be removably affixed to a base having ground wheels particularly suited for transportation over a ground surface for positioning said hand hygiene module 1100 at, near, or within, any region, location, zone, realm, or other area where microorganisms reside, including hospital rooms, doctors' offices, hospital waiting rooms, hospital entrance ways, emergency rooms, operating rooms, incubator rooms, hospital hallways, hospital dining facilities, as well as anywhere within preschools, elementary schools, middle schools, high schools, bowling alleys, churches, and pet stores, to name only a few. The hand hygiene module 1100 is uniquely capable of being positioned in any place with heightened risk of contamination, for whatever reason or source, through the deployment and exercise of ground wheels configured for mobile transportation. The ground wheels are disposed on the main structural assembly of the portable hand hygiene module. The main structural assembly includes a frame formed from a stem, said stem coupled at a proximal end with said support base. The ground wheels are additionally coupled in mechanical communication with locking members (not shown) to prevent the hand hygiene module 1100 from actively or passively rolling during a hand hygiene event. Providing a portable hand hygiene module 1100 near a patient encourages longer hand sanitization event because the health care worker can spend time talking to the patient while they are sanitizing, thereby encouraging hand sanitization.

Compliance data which is gathered and stored from badges 800 within the relevant service area and may be transmitted to the service area module 1400 which in turn transmits the information to the centralized computer.

The body couples with a teaching surface 1104 configured to draw attention to the hand hygiene module and to teach a plurality of hand hygiene steps. The body 1108 includes a translucent portion 1106 for viewing the amount of sanitizer solution remaining in the hand hygiene module 1100. A sensor 1112 coupled to a lower portion 1110 of the hand hygiene module 1100 captures hand movement of the person interacting with the hand hygiene module 100 causing a quantity of hand sanitizer to dispense into one or both of the person's hands. An emitter 1116 wirelessly sends, via ultrasonic or any other communication technology, a query as to whether a person is detected by a sensor 1114 to, for example, a receiver. The badge 800 shown in FIG. 8 may respond when queried. The response by the badge 800 may be heard by the sensor 1114 or another sensor on the hand hygiene module 1100 implemented for receiving a query response from the badge 800. The hand hygiene module 1100 may additionally include an IR sensor for communicating with a remote device for manually adjusting attention variable features of the present invention, such as adjusting attention stimuli, adjusting system settings, and the like. Either of the hand hygiene module and the badge 800 includes a plurality of time interval units 804 that may be formed as a plurality of colored lights, including, without limitation, green, yellow, amber, and red lights to show the duration of the sanitization event. Elements other than lights can perform the task of indicating this information and are within the spirit and scope of the present invention. In some embodiments, the hand hygiene badge 800 includes a microphone for sensing queries. Further the microphone may sense and receive data requests. The requests may be communicated from the microphone to the microprocessor of the hand hygiene badge 800.

In one embodiment, the body 1108 is configured to open to allow for replacement of hand sanitizers and to access the internal components of the hand hygiene module. However, in some embodiments, the body 1108 is securely closed with a lock for preventing tampering with the hand sanitizer and/or internal components. In some embodiments, the body is secured closed with a lock, such as a magnetic lock.

Figure 13:
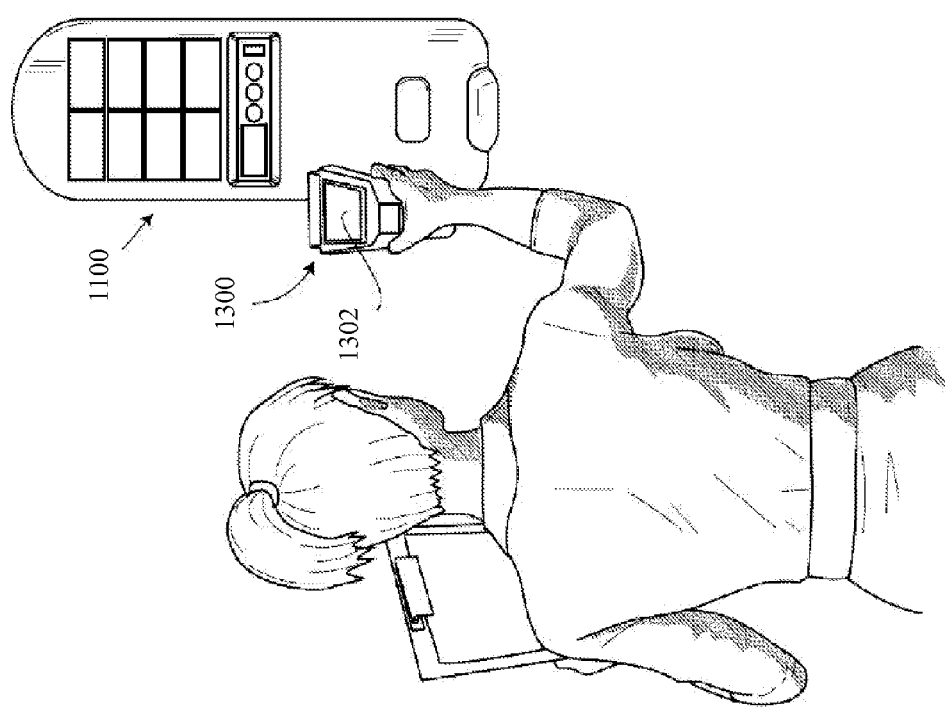
FIG. 13 illustrates a partial perspective view of the hand hygiene module of FIG. 11 interacting with a remote device for calibrating the device.

Referring now to FIG. 13, a partial perspective view of the hand hygiene module 1100 of FIG. 11 is illustrated depicting a remote calibration device 1300 that interacts with the hand hygiene module 1100. The remote calibration device 1300 may be used to change calibrations at the command of authorized staff using a remotely situated computer. The information that is programmed to change the calibrations is sent to the hand hygiene module 1100. The calibration may depend on the environment where the hand hygiene module 1100 is placed. For example, a hand hygiene module 1100 placed outside of a bank elevator is configured to use motion sensing to detect persons exiting the elevator. The hand hygiene module 1100 can additionally be configured to output messages, such as "elevators are a common source of bacterial infection" or "sanitize your hands to protect your family at home." The calibration may be done automatically by a calibration device, otherwise known as a remote calibration device 1300. The calibration settings are set and/or approved by a staff member. The calibration settings may be entered into a centralized computer and provided to the remote calibration device 1300. Then a staff member may use the remote member 1300 for calibrating the hand hygiene modules. For example, the remote calibration device 1300 may be used to adjust the volume of hand hygiene messages, which may be the result of a noncompliant hand hygiene event. The remote calibration device 1300 may be used to turn off an alarm sounding on the hand hygiene module 1100. The remote calibration device 1300 may display information on a remote display device 1302. The displayed information may include, for instance, battery life and compliance statistics. The remote calibration device 1300 may receive badge information tied to noncompliant hand hygiene events. The remote device may receive badge information tied to compliant hand hygiene events. In some embodiments, the remote calibration device 1300 may include a checklist of the devices that need to be placed in communication, thereby indicating to the staff member to facilitate communication between the remote calibration device 1300 and one or more hand hygiene modules 1100. The communication may include sending and receiving information between the remote calibration device 1300 and the one or more hand hygiene modules 1100. The hand hygiene module 1100 may receive calibration information from the remote calibration device 1300.

FIG. 14 is a perspective front view of a portable service area module 1400 for placement within each service area. The device does not need to be wall mounted or coupled with an electrical outlet. The portable service area module 1400 may include a phone that receives and downloads information sent from the remote calibration device 1300 and/or the centralized computer, including information sent at the command of an authorized staff member. The information received at the service area module 1400 may include calibration settings for stimulating engagement through psychological and social pressure to hand sanitize. The service area module 1400 may provide calibration information to the remote calibration device 1300, which, in turn, allows the remote calibration device 1300 to be used by staff members to calibrate the hand hygiene modules. The service area module 1400 may alert the staff of a need to distribute calibration settings from the remote computer, through the calibration device 1300 and the remote calibration device 1300 to one or more hand hygiene modules.

The phone 1402 may be a corded or cordless phone. The phone 1402 may be set within a recess 1404. A flashing light (not shown) coupled with the portable hand hygiene module, other visual stimuli, or audible stimuli, may indicate an incoming and/or outgoing call. The portable service area module 1400 includes a portion 1406 equipped with a holster with a USB data transmission port and power supply. The portion 1406 or other similar ports on the portable service area module 1400 can be used for transmitting data and/or charging a number of peripheral devices, such as cellphones, tablet computing devices, and others. The portable service area module 1400 additionally includes a display 1408 for displaying messages from the centralized computer which may be provided by the infection control staff. The portable service area module 1400 shown in FIG. 14 is particularly suited for transportation over a ground surface for positioning said portable service area module 1400 at, near, or within, any region, location, zone, realm, or other area where microorganisms reside, including hospital rooms, doctors' offices, hospital waiting rooms, hospital entrance ways, emergency rooms, operating rooms, incubator rooms, hospital hallways, hospital dining facilities, as well as anywhere within preschools, elementary schools, middle schools, high schools, bowling alleys, churches, and pet stores, to name only a few. The portable service area module 1400 is uniquely capable of being positioned in bacterial rich areas through the deployment and exercise of ground wheels 1410 configured for mobile transportation. The ground wheels 1410 are disposed on the base 1412. In the embodiment shown in FIG. 14, the base 1412 includes a stem 1414. In some embodiments, the stem length can be adjusted to lower or raise the height of the portable service area module 1400. Compliance data is gathered and stored from badges 800 within the relevant service area. A dedicated phone 1402 connects directly and only to the infection control staff. The dedicated phone 1402 is similar to a hotline that provides a connection between infection control staff and other staff members. The additional purpose of the dedicated phone 1402 allows a line for infection control staff to directly inform responsible area personnel of a hand sanitization compliance levels. The dedicated phone 1402 allows service area staff to directly contact, through a dedicated phone line, infection control staff for the purpose of informing the infection control staff that a hand hygiene module, such as a hand hygiene module placed in a patient's room, should be calibrated or otherwise altered. For patients with a particularly infectious disease, the infection control staff can quickly be informed of the need to adjust the hand hygiene modules within a particular distance to the patient. The phone may be used by hospital (or other institution) staff to inform competent staff of a changed situation which may warrant a change in calibration of devices or to request additional information, etc.

The ground wheels 1410 allow the hand sanitizing device to be moved directly next to the patient's bed. Studies have shown that patients confined to bed have a much lower incidence of HAI if provided with hand sanitation in their immediate area. For example, when being served food, the dispenser is available to the server. Having the device in such close proximity to the patient/bed allows the patient to observe whether others are sanitizing their hands and whether or not they are complying with suggested hand sanitization procedures.

Figure 15:
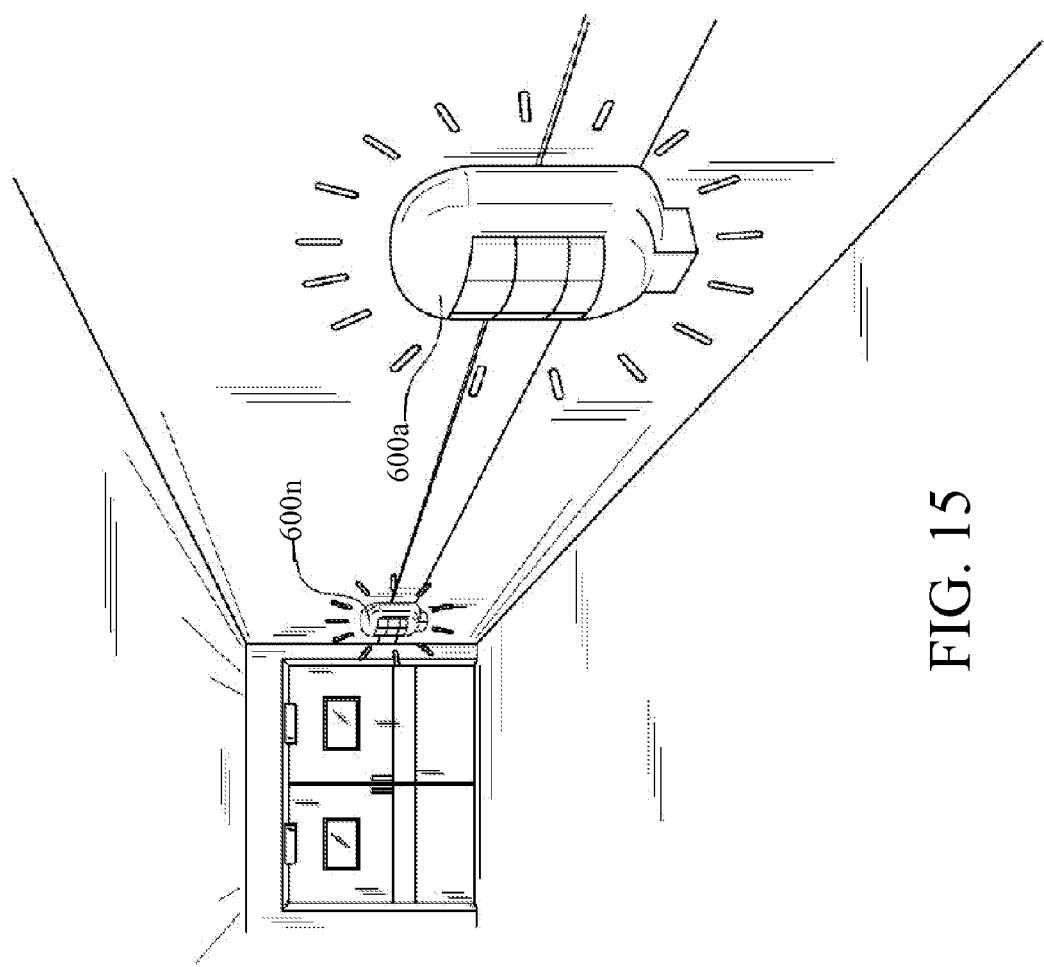
FIG. 15 illustrates placement of a plurality of hand hygiene modules at one exemplary ingress/egress locations.

FIG. 15 illustrates placement of a plurality of hand hygiene modules 600a-600n, where "n" indicates any number greater than 1, at an exemplary ingress/egress locations. The plurality of hand hygiene modules may each individually communicate with the remote calibration device 1300 shown in FIG. 13. The plurality of hand hygiene modules 600 may additionally communicate with a plurality of badges 800, as shown in FIG. 8.

In some embodiments, the hand hygiene modules 100, 600, 1100 provide communication means for communication with a server, a database, a remote device, and/or a badge. The communication means may include any known communication means and include necessary components, including one or more antennas.

In some embodiments, the hand hygiene modules 100, 600, 1100 provide USB ports for communication, data transmission, and/or calibration of the hand hygiene modules in accordance with the spirit and scope of the present invention. The invention may include flashing lights (not pictured) to alert to the need to calibrate the hand hygiene module. In some embodiments, the present invention may include buzzers, warblers, ringers, or the like, for alerting of the need to calibrate the hand hygiene module.

In some embodiments, the display screen (or any other communication components) of the hand hygiene modules 100, 600, 1100 may display or otherwise communicate successful calibration of the hand hygiene module. In some embodiments, the display screen (or any other communication components) of the hand hygiene modules 100, 600, 1100 may display or otherwise communicate any definable average of successful calibration of the hand hygiene module of all persons that have used the hand hygiene module or a combination of such persons.

In some embodiments, the hand hygiene badge may communicate with the hand hygiene module and other sensors regardless of which side of the badge is facing outward from the wearer. For example, the badge may include IR remote communication elements on both the front and the back of the badge thereby preventing wearers from attempting to defeat device hand hygiene badge 800 detection. Alternatively, the badge may include QR codes on the front and the back of the hand hygiene badge 800. Alternatively, an RFID communication device allows communication regardless of the badge orientation on the wearer.

In some embodiments, the badge may include a time interval module (not shown). The time interval module may include time interval units 804. The time interval units 804 may include one or more lights. The time interval module is configured to count down or up a time interval until a hand hygiene event is recommended and/or required. The time interval module causes the time interval units 804 to turn off sequentially to provide a progressive counter for indicating to the badge wearer, or other hospital staff, of the need to sanitize their hands. For example, some of the lights may be green, some yellow, and some red. The green lights may first turn off as time passes. Subsequently, the yellow lights may turn off. When only the red light is turned on, the badge indicates the present need for a person to engage a hand hygiene module and sanitize their hands. In some embodiments, the hand hygiene module may alter the time interval units 804 to indicate an immediate need for a hand hygiene event. This may occur, for example, when the doctor enters or exits the room of a high risk patient, during flu season, or during epidemics, to name a few instances.

In an alternative embodiment, the time interval unit 804 may alternatively cause the lights to turn on. For example, the first green light may be turned on. As time passes, the yellow lights may turn on. As more time passes, the red lights may turn on, thereby indicating a present need to for a person to engage a hand hygiene module.

In an alternative embodiment, time interval unit 804 may cause lights to flash or otherwise signal to the hospital staff, the wearer, or even the patient, of the wearer's need to sanitize their hands. This allows the patient to actively monitor the hand sanitization of the hospital staff who interact with the patient and allows the patient to become actively involved in protecting against contracting HAIs.

In some embodiments, the lights may indicate the hand hygiene event thoroughness and/or effectiveness. The lights may indicate the average time spent sanitizing. For example, a green light may indicate fifteen or more seconds of sanitizing. A yellow light may indicate ten or more seconds of sanitizing. Amber may indicate five or more seconds of sanitizing. Red may indicate 5 or less seconds of sanitizing. It is contemplated that the number of seconds required to cause a particular color indicia on the hand hygiene badge may be altered according to determined health requirements. In some embodiments, a sensor on the hand hygiene module determines the appropriate length of time for the hand hygiene event, which then communicates this data to the badge 800. In some embodiments, the hand hygiene module monitors the length of time in front of the unit and from there, any of the devices specified herein could measure the average amount of time spent in front of the hand hygiene module. In some embodiments, colored lights on one or both of the hand hygiene module and the badge 800 are reset. In some embodiments, the resetting of the colored lights is performed by way of authorized staff interaction. In some embodiments, the color lights indicate an average amount of time that the badge 800 spent in front of the hand hygiene module until the point of colored light reset.

In some embodiments, the hand hygiene badge 800 (a wearable device) communicates with a hand hygiene module 100, 600. The hand hygiene module 100, 600 causes the lights on the badge 800 to reset subsequent to a compliant hand hygiene event. For instance, the hand hygiene module 800 will recognize that the person wearing the badge has sanitized their hands for an appropriately determined period of time. The hand hygiene modules 700, 1100 may send a digital reset signal to the badge 800. The hand hygiene badge 800 receives the reset signal from the hand hygiene module 700, 1100 thereby resetting the time interval unit 804 and switching at least some of the lights 804 between an on and off position. The hand hygiene badge 800 is reset causing the badge to start a new countdown for indicating the need for a subsequent hand hygiene event. The hand hygiene badge 800 shall start a new timing sequence at the time interval unit 804 for indicating the time until a subsequent hand hygiene event is required.

What is claimed is:
1. A method for improving hand hygiene compliance comprising:
   providing a sanitizer dispensing device;
   providing an attention stimulus operably configured to draw the attention of a user to the sanitizer dispensing device and varying the attention stimulus based on an environmental factor, the environmental factor including at least one of: a time of year, and a flu or cold season;
   identifying the user's initiation of a use by the user of the sanitizer dispensing device to sanitize a hand of the user; and
   actively sequentially providing a plurality of stimuli to the user during the user's use of the sanitizer dispensing device to sanitize the user's hand, the plurality of stimuli including at least one of an audible signal and a visual signal and actively sequentially instructing the user to perform each of a plurality of hygiene steps.
2. The method according to claim 1, further comprising:
   electronically monitoring a compliance by the user with the plurality of hygiene steps by at least one of:
     recording whether the user performed the plurality of hygiene steps;
     communicating an indicator of whether the user performed the plurality of hygiene steps; and displaying the indicator of whether the user performed the plurality of hygiene steps, wherein the user's compliance is defined as the user performing the plurality of hygiene steps.

3. The method according to claim 2, wherein the indicator includes at least one of a user-compliant indication and a user noncompliant indication.

4. The method according to claim 2, further comprising:
communicating with a wearable device, the wearable device worn by the user and having a visual indicia with at least two states; and
placing the wearable device into one of the at least two states after electronically monitoring the user's compliance.

5. The method according to claim 1 further comprising:
providing a wearable device, the wearable device worn by the user; and
subsequent to the instructing the user to perform the plurality of hygiene steps, providing with the wearable device an indication of the user's compliance.

6. The method according to claim 1, wherein the actively sequentially providing a plurality of stimuli includes:
sequentially providing an active step attention stimulus corresponding to each of the plurality of hygiene steps.

7. The method according to claim 1, further comprising:
providing a plurality of sanitizer dispensing devices including the sanitizer dispensing device, each of the plurality of sanitizer dispensing devices arranged along a path and providing an attention stimulus, the attention stimulus of a first one of the plurality of sanitizer dispensing devices being different from the attention stimulus of a second of the plurality of dispensing devices.

8. A method for improving hand hygiene compliance comprising:
providing a first stimulus to a user to initiate a hand hygiene event by the user, the hand hygiene event having a plurality of hand hygiene steps, the first stimulus including at least one of an audible signal and a visual signal;
adjusting the first stimulus based on a location of a sanitizer dispensing device associated with the first stimulus;
identifying an initiation by the user of a use by the user of the sanitizer dispensing device to engage in the hand hygiene event;
actively sequentially providing a plurality of second stimuli to the user during the user's use of the sanitizer dispensing device to engage in the hand hygiene event, the plurality of second stimuli including at least one of an audible signal and a visual signal and actively sequentially instructing the user to perform the plurality of hand hygiene steps;
monitoring whether the user performed the plurality of hand hygiene steps; and
alerting as to whether the user performed the plurality of hygiene steps.

9. The method according to claim 8, further comprising:
providing a wearable device worn by the user; and
communicating to the wearable device the alert as to whether the user performed the plurality of hygiene steps.

10. The method according to claim 8, further comprising:
instructing the user as to what hand motion to use for each of the plurality of hand hygiene steps.

11. The method according to claim 8, further comprising:
alerting the user of a need to initiate a subsequent hand hygiene step after the user's performance of at least one of the plurality of hand hygiene steps.

12. A system for facilitating and monitoring a hand hygiene, the system comprising:
a hand sanitizer dispensing device;
a thermal imager operably configured to detect individuals with pyrexia; and
a display operable to actively and sequentially display a plurality of stimuli to a user during a use by the user of the hand sanitizer dispensing device, the plurality of stimuli actively sequentially instructing the user to perform each of a plurality of hygiene steps.

13. The system according to claim 12, further comprising:
a detector operable to detect whether the user performed the plurality of hand hygiene steps.

14. The system according to claim 12, further comprising:
a hand hygiene module; and
a wearable device having:
a receiver operable to receive information from the hand hygiene module, the information identifying a compliance by the user with the plurality of hand hygiene steps, the user's compliance defined by whether the user performed the plurality of hand hygiene steps; and
at least one indicator operable to communicate the user's compliance.

15. The system according to claim 14, wherein the wearable device further includes:
a timer, and
the at least one indicator is operable to indicate that an elapsed amount of time has passed since a previous compliance by the user, the user's previous compliance defined by whether the user performed the plurality of hand hygiene steps during a previous use by the user of the hand sanitizer dispensing device.

16. The system according to claim 12, further comprising:
a second display operable to display an indicator of a compliance by the user, the user's compliance defined by whether the user performed the plurality of hygiene steps.

17. A system for facilitating and monitoring a hand hygiene process, the system comprising:
a hand sanitizer dispensing device;
a display operable to actively and sequentially display a plurality of stimuli to a user during a use by the user of the hand sanitizer dispensing device to engage in a hand hygiene event, the plurality of stimuli actively sequentially instructing the user to perform each of a plurality of hygiene steps;
a wearable device dispensing module; and
a controller operable to prevent the wearable device dispensing module from dispensing a wearable device until subsequent to a detection of a compliance by the user, the user's compliance defined by whether the user performed the plurality of hand hygiene steps.

* * * * *